United States Patent [19]
Garcia-Roel et al.

[11] 3,954,103
[45] May 4, 1976

[54] APPARATUS AND INTRAUTERINE DEVICE FOR THE IMMEDIATE PUERPERIUM FOR THE CONTROL OF HUMAN FERTILITY

[76] Inventors: Ricardo Garcia-Roel; Ruben Saldaña-Garcia; Rogelio F. Garcia-Flores, all of Escobedo Sur 733, Suite 201, Monterrey, Nuevo Leon, Mexico

[22] Filed: Dec. 9, 1974

[21] Appl. No.: 530,847

[52] U.S. Cl. .............................. 128/130; 128/330
[51] Int. Cl.² ................................. A61F 5/46
[58] Field of Search .......................................
128/127–131, 329, 330, 362

[56] References Cited
UNITED STATES PATENTS

| | | | |
|---|---|---|---|
| 3,598,115 | 8/1971 | Horne | 128/130 |
| 3,675,639 | 7/1972 | Cimber | 128/130 |
| 3,809,076 | 5/1974 | Chabon | 128/130 |

*Primary Examiner*—Lawrence W. Trapp
*Attorney, Agent, or Firm*—Laurence R. Brown

[57] ABSTRACT

Contraceptive intrauterine means is constructed to permit a surgeon when the uterine cavity is enlarged after birth to manually attach a foreign object to the uterine cavity wall by a hook, coupled thereto, thereby to control fertility. A truncated cylindrical member fits on the surgeon's finger for movement axially in a concentric outer cylindrical guide when a detent position is overcome by manual force as the guide frontal portion engages the uterine wall. The hook is removably attached to the truncated cylindrical member so that as it moves to a position beyond the guide it can become embedded into the uterine wall and the cylindrical members are removed leaving the intrauterine means in place.

4 Claims, 10 Drawing Figures

APPARATUS AND INTRAUTERINE DEVICE FOR THE IMMEDIATE PUERPERIUM FOR THE CONTROL OF HUMAN FERTILITY

The present invention refers to an intrauterine device for the immediate puerperium for the control of human fertility, in which the combination of the means which make it up permit its presence in the uterine cavity at any time, with the advantage of not being expelled from said cavity when its insertion is done in the immediate post-partum or during a cesarean operation.

The purpose of the present invention is to avoid the inconveniences of the devices used up to date, which should only be inserted in the uterus when it is in its normal state, since if they were to be inserted when the uterine cavity is enlarged after birth, it is certain that before the uterus were to take its original state, the device would have been expelled due to the dimensions which the uterus has in that state of hypertrophy.

Another of the purposes of the present invention is to foresee a means so that once the device is in place in the uterine cavity, and once the uterus has reduced its size until it arrives at its normal dimensions, the device be provided with sufficient mechanical means to avoid its expulsion from the uterine cavity and consequently the effort of placing it is not wasted.

The characteristic details of the present invention are clearly shown in the following description and in the drawings which accompany it as an illustration of it and the same reference signs are used to indicate the same parts in the figures shown.

Figure 1:
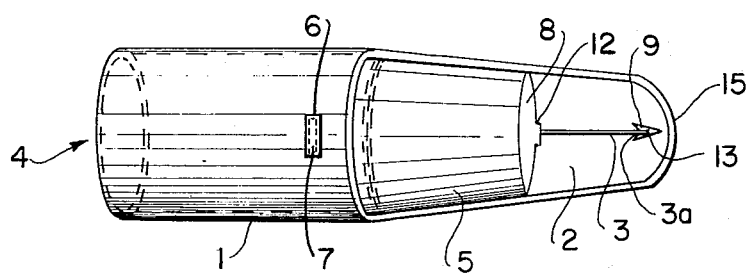
FIG. 1 shows a conventional view of the unit made up of a protecting sleeve and guide, the applicator and the device.
Figure 2:
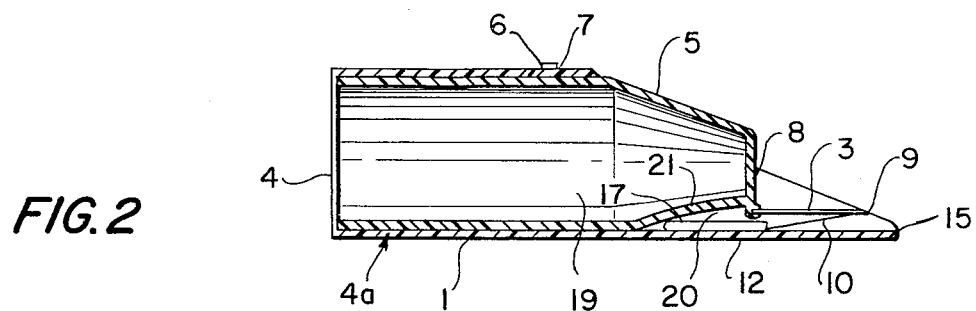
FIG. 2 shows a longitudinal cross section view of the protecting sleeve and guide, the applicator and the mounted device.
Figure 3:
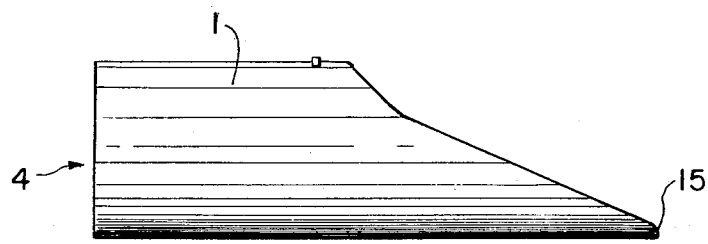
FIG. 3 shows a side view of the sleeve.
Figure 4:
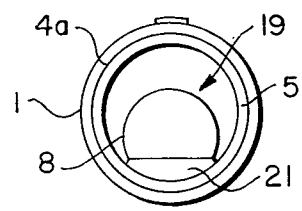
FIG. 4 shows an end view of the sleeve.
Figure 5:
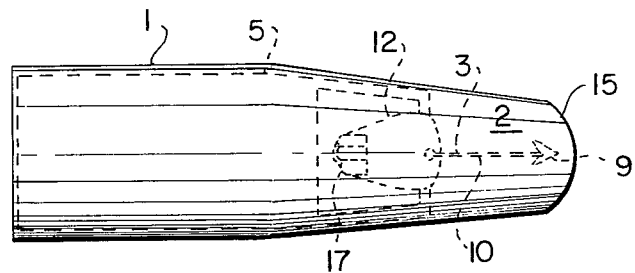
FIG. 5 shows a top view of the sleeve and the applicator.
Figure 6:
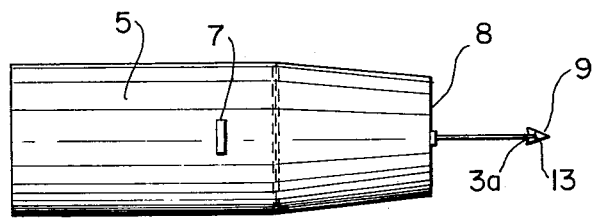
FIG. 6 shows an anterior view of the applicator.
Figure 7:
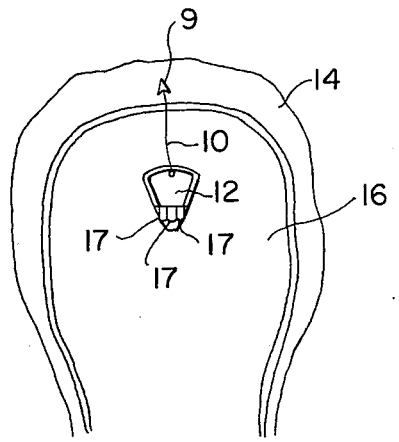
FIG. 7 shows a partially transversal cross section view of the enlarged uterus with the recently placed device.
Figure 8:
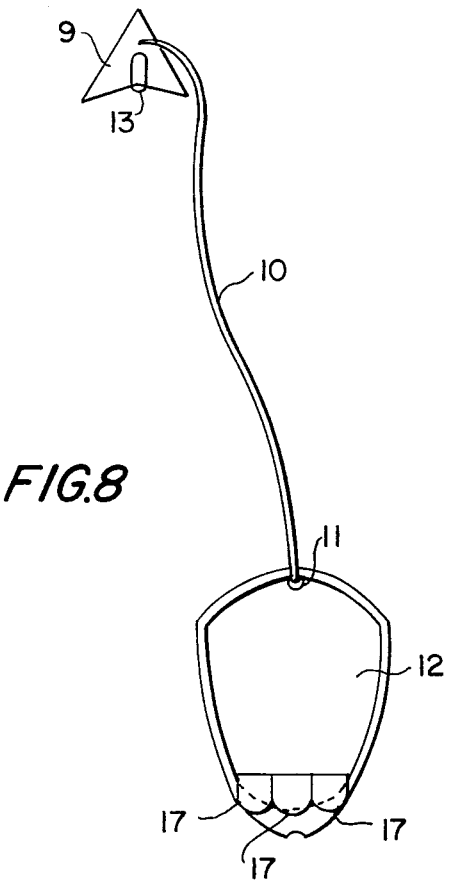
FIG. 8 shows a conventional view of the unit, hook, strap, ring and tab of the device.
Figure 9:
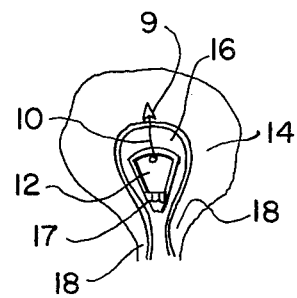
FIG. 9 shows a partial cross section view of the uterus and the device.
Figure 10:
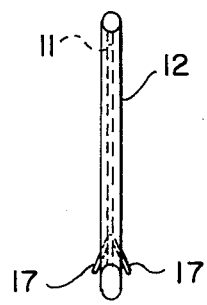
FIG. 10 shows a side view of the tab showing the eyelets.

With reference to said figures, this device is formed by the combination of a protecting sleeve, manufactured preferably of appropriate plastic material whose body in the form of an outer cylindrical member 1 is joined to a frontal portion guide 2 the purpose of which it is to serve as covering and guide for the needle 3 headed in such a manner that it 3 not be accidentally inserted in some other tissue before it arrives at the place in which it ought to be duly placed. The body 1 has in its interior a hollow 4 in the interior of which the truncated cylinder 5 is housed which forms the body of the applicator, with the understanding that the diameter of the cylinder 5 shall have the necessary dimensions to penetrate the hollow 4. When the interior face 4-A of the body 1 enters hollow 4 there ought to be sufficient contact so there be no play which would result in the accidental exit of the cylinder 5.

The body 1 has in its interior part a slit 6 into which a detent edge 7 of cylinder 5 shall be inserted whereby the cylinder 5 shall remain fixed in the cavity 4.

The cylinder 5 which shall also be preferably manufactured of appropriate plastic material, has a platform 8 upon which the needle 3 is placed and affixed by appropriate means to said platform 8 a cavity 19 is found in the interior of the cylinder which allows at a given time the insertion of the surgeon's finger in order to proceed to place the device by said needle 3 by the hook 9. The hook has affixed by appropriate means the strap 10 which joins the foreign body to be held in the uterine cavity termed herein tab 12 through the ring 11 to the said hook 9. The hook 9 has a blind duct 13 to which shall be inserted the point 3-A of the needle 3 in such a way that when the hook 9 is inserted in the uterine wall 14, the needle 3 can be removed but the hook 9 shall be fixed in the uterine wall 14 and consequently the expulsion of the device formed by the hook 9, strap 10 and tab 12 is impossible.

Meanwhile the cylinder 5 as found coupled in the interior of the body 1, has tab 12 in the housing 20 which is formed as a consequence of a curvature 21 of the cylinder 5 in its upper rear part, so as to keep the tab 12 from dislodging itself which would cause serious inconveniences.

The placing of the device in the uterine wall 14 and inside the uterus, is to be done manually, first the device shall be placed on the surgeon's index or middle finger using for this purpose the cavity 19 of the cylinder 5, then the device is introduced through the neck of the uterus until the extreme front 15 of the guide 2 touches the end of the uterine cavity 14, then with a quick movement the hook 9 is inserted pressing for this purpose the cylinder 5 which as a result would free the detent edge 7 from the slit 6 and move cylinder 5 toward front 15 carrying the needle 3 to protude the frontal limit 15 of the guide 2 so that the hook 9 would first make contact and then penetrate the uterine wall 14; once this is done, the sleeve formed by the body 1 and the guide 2 would be removed as well as the cylinder 5 and the needle 3 which is attached to the cylinder 5, leaving the hook 9 alone affixed to the uterine wall 14 and hanging from it, the strap 10 and the tab 12.

The above described operation is done in the immediate post-partum or during a cesarean operation, it is obvious that due to the dimensions which the uterine cavity 16 has at those times, the tab 12 shall be left hanging in the uterine cavity 16; as time passes and the cavity 16 is reduced, the device will be squeezed and it is possible that the uterus will tend to expel the device and it will be at this time when the flanges 17 will become activated so that as they are squeezed against the uterine wall 18 they will tend to open thus preventing the expulsion of the device for which purpose the strap 10 which is held by the hook 9 will cooperate.

It is a scientifically proven fact that as long as a foreign body exists in the uterus, there is practically no possibility of conception, so that the presence of the device makes almost certain the impossibility of a pregnancy.

There is the possibility that if with the passing of time the woman who has had the device wishes to become pregnant once again, all she has to do is to allow the removal of the device through traction with pliers and the quick dislodging of the hook 9.

What I claimed is:

1. Contraceptive intrauterine means for manually inserting a foreign object in the uterine cavity when enlarged after birth, comprising in combination, a cylindrical guide, (sleeve) truncated cylinder means for disposal on a surgeon's finger, guidable within said guide, an assembly including a hook removably held on said truncated cylinder, said guide having a frontal limit to shield the hook from premature engagement with the uterine wall and a tab coupled to said hook comprising said foreign object, and a detent holding said truncated cylinder in place with said hook in shielded position, said truncated cylinder comprising means for displacing by manual force said hook beyond said frontal limit thereby attaching said hook to said uterine wall to deposit said foreign object in said uterine cavity.

2. Means as defined in claim 1, wherein said hook is removably held on a separable needle engaging said hook and extending said needle and hook from said truncated cylinder.

3. Means as defined in claim 1, wherein said tab is coupled to said hook by a strap.

4. Means as defined in claim 1, wherein said tab comprises a plastic ring with flanges activated when the device is squeezed by the uterine wall to provide means preventing expulsion from the uterine cavity.

* * * * *